United States Patent [19]

Gallagher

[11] Patent Number: 5,363,691
[45] Date of Patent: Nov. 15, 1994

[54] VIBRATILE SENSING INSTRUMENT

[75] Inventor: John G. Gallagher, Old Malton, England

[73] Assignee: Hydramotion Limited, Malton, United Kingdom

[21] Appl. No.: 39,194

[22] PCT Filed: Sep. 20, 1991

[86] PCT No.: PCT/GB91/01623

§ 371 Date: Apr. 14, 1993

§ 102(e) Date: Apr. 14, 1993

[87] PCT Pub. No.: WO92/05421

PCT Pub. Date: Apr. 2, 1992

[30] Foreign Application Priority Data

Sep. 24, 1990 [GB] United Kingdom ............... 9020771
Mar. 4, 1991 [GB] United Kingdom ............... 9104539

[51] Int. Cl.[5] .................. G01N 9/00; G01N 11/16
[52] U.S. Cl. ......................... 73/32 A; 73/579; 73/30.01; 73/702
[58] Field of Search ............. 73/32 A, 30.01, 30.04, 73/31.05, 579, 581, 702, 704, DIG. 1, 66 B, 664, 668

[56] References Cited

U.S. PATENT DOCUMENTS

| 3,665,752 | 5/1972 | Piper | 73/32 |
| 3,878,710 | 4/1975 | Miller | 73/32 A |
| 3,926,035 | 12/1975 | Schlatter | 73/32 |
| 4,114,423 | 9/1978 | Wenger | 73/30 |
| 4,297,872 | 11/1981 | Ikeda et al. | 73/32 |
| 4,409,840 | 10/1983 | Roberts | 73/704 |
| 4,420,983 | 12/1983 | Langdon | 73/32 A |

FOREIGN PATENT DOCUMENTS

| 331538 | 1/1989 | European Pat. Off. |
| 2027539 | 2/1980 | United Kingdom |
| WO90/02933 | 3/1990 | WIPO |

OTHER PUBLICATIONS

Control and Instrumentation, vol. 7, No. 22, Feb. 1975, D. Green, "resonance frequency: measurement top of the seventies", pp. 40-43.

Primary Examiner—Tom Noland
Assistant Examiner—Helen C. Kwok
Attorney, Agent, or Firm—Nixon & Vanderhye

[57] ABSTRACT

An instrument for the detection or measurement of attributes of a material comprises at least one vane which is mounted on a support that allows the vane to vibrate, a drive transducer which is disposed relative to the vane to stimulate vibration therein and at least one sensing transducer disposed to sense the vibrations.

15 Claims, 3 Drawing Sheets

VIBRATILE SENSING INSTRUMENT

BACKGROUND OF THE INVENTION

This invention relates to the detection or measurement of attributes of materials generally, for example density, flow rate, moisture content or other attributes or parameters of flowable materials, such as gaseous or liquid fluids, emulsions, particulate or granulate materials or suspensions of solids in liquids, such as a slurry.

A wide variety of devices for such detection and measurement are known in the art. Most of them are specific to a particular attribute or parameter. The general object of the present invention is to provide a reliable and versatile device which can generally be used for a measurement of a variety of different attributes.

The state of the art is represented by GB-A-2222683, which describes a sensor that externally resembles a preferred embodiment of the invention but operates rather differently. The sensor described in GB-A-2222683 comprises an elongate support, preferably in the form of a shaft carrying, preferably near one end, a plurality of laterally extending fins or vanes constituting capacitor plates. The vanes protrude laterally from the support but are generally elongate. The sensor includes circuits responsive to the capacitance between pairs of plates in order to derive an indication of a property, such as moisture content, of the material which is disposed between the plates or fins when the sensor is immersed in that material.

A capacitive technique, like most measurements of moisture, is essentially a measurement of two volumetric ratios. However most definitions of moisture content are by ratio of mass. Although, for example, water density over a wide temperature range is well known, it is also necessary to know the bulk density of the true moisture content by mass to be measured.

The present invention is based on the exploitation of the fact that when a fin or vane is stimulated into small vibrations it has degrees of freedom in two planes, along and across the vane. It obeys a second order rave equation resulting in standing waves set up along the vane. If such a vane is immersed in a flowable material, it is found that the square root of the frequency of oscillation is inversely related to the density of the surrounding medium. However, analysis of wave equation solutions indicates that there is a much greater number of resonant modes and frequencies than are present in, for example, a vibrating tube densitometer. Accordingly, the resonant properties allow exploitation beyond the mere scope of density measurement.

Broadly, according to the invention, an instrument for the detection or measurement of attributes of a material comprises at least one vane which is mounted on a support that allows the vane to vibrate, a drive transducer which is disposed relative to the vane to stimulate vibration therein and at least one sensing transducer disposed to sense said vibrations.

In preferred embodiments of the invention the support is elongate. The vane may comprise a fin which protrudes laterally from the support. However, many other configurations are feasible.

Where the vane is elongate, the said transducers may be spaced apart along the length of the vane. A sensing transducer may be disposed at substantially an antinode of the vibration of the vane. The support may engage the vane at at least one region corresponding to a node of the vibration. In particular, there may be means for clamping the vane near a median region and the drive transducer may be disposed to induce a vibration in a plane transverse the median line.

At least one of the transducers may be disposed on a peninsular portion within the vane. The peninsular portion may be formed as a partly cutout tab which lies in the local plane of the vane. The vane may be clamped between such a peninsular portion and an adjacent part of the vane so that the peninsular portions and adjacent portions each constitute a cantilever. This is useful both for the induction of vibration in and the sensing of vibrations in the vane. The said one transducer may be a drive transducer and the peninsular portion on which the drive transducer is disposed may carry a substantial mass. Where the vane is clamped near the median region, the various transducers may each be disposed on a respective peninsular portion positioned in the median region and spaced apart along it.

By itself a drive transducer might be insufficient to induce vibrations of sufficient amplitude in the vane, and accordingly it is generally desirable to provide a regenerative or positive feedback coupling from the sensing transducer, or one of the sensing transducers, to the drive transducer. This coupling may include a bandpass filter for the rejection of signals other than those associated with a principal or desired mode of vibration of the vane.

As will be explained hereinafter, a useful output may be represented by the output frequency of a sensing transducer or may be obtained by comparing the phase of signals at the drive transducer and one of the sensing transducers or may be obtained by comparison of the amplitude, frequency or phase of the outputs of two sensing transducers disposed at different positions on the vane, for example at antinodes of vibration thereof.

DETAILED DESCRIPTION OF A PREFERRED EMBODIMENT

Figure 1:
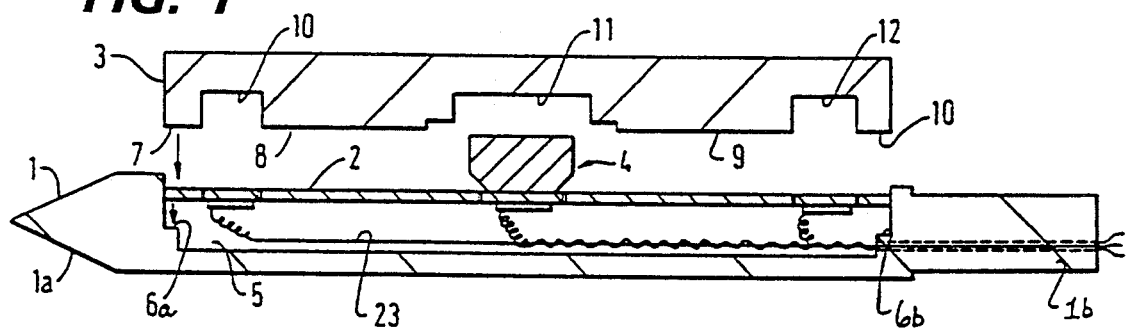
FIG. 1 illustrates sectionally an embodiment of the invention in partly assembled form.
Figure 2:
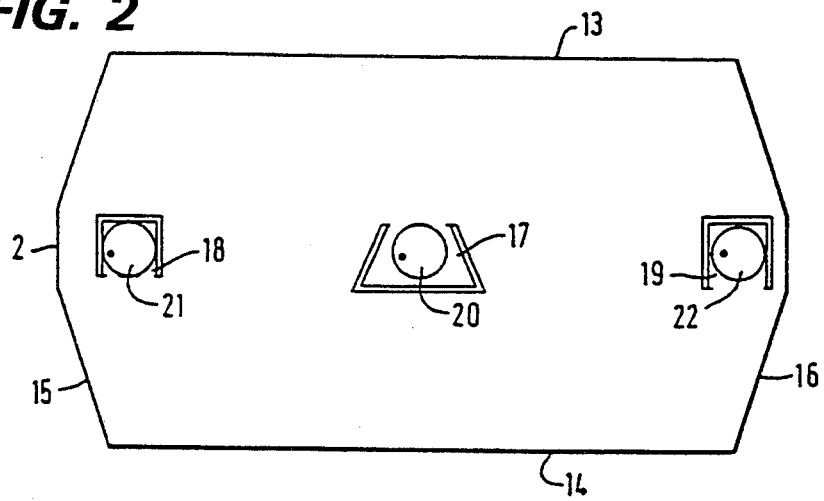
FIG. 2 illustrates a vane forming part of the embodiment shown in FIG. 1.
Figure 5:
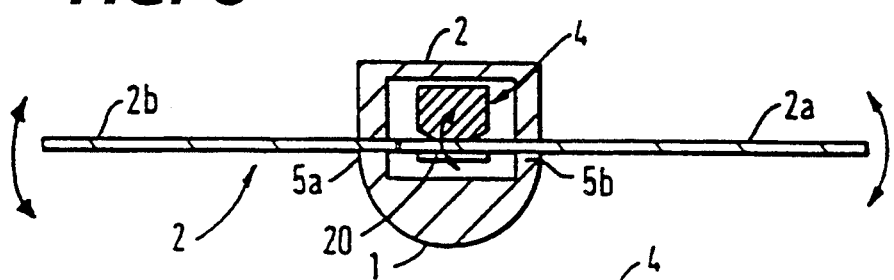
FIG. 5 illustrates a lateral cross-section through the embodiment illustrated in the previous Figures.

The device or sensor shown principally in FIGS. 1, 2 and 5 includes a support 1 which may be in the form of an elongate body which may have a pointed or tapering leading end 1a so that the device is adapted, if desired, for insertion into flowable material. However, other configurations of the body are possible. The support may be streamlined where the device is intended for use in a fluid flow.

The support 1 supports at least one vane which in this embodiment of the invention is configured to provide a pair of fins which protrude laterally from the support. The vane 2 is held in place within the support 1 by means of a clamp member 3 which fits into and constitutes part of the support. The support 1 has a longitudinal recess 5. The recess 5 has two longitudinal side walls 5a and 5b and end shoulders 6a and 6b so that the vane is in this embodiment of the invention clamped by the clamp member 3 along two lines extending parallel and adjacent to a median line of the vane.

The clamp member 3 has flat underportions 7, 8, 9 and 10 which engage the shoulders 6a, 6b and the sidewall portions 5a and 5b so as not only to clamp the vane but also to define an interior recess in which various transducers and electrical connections to them are disposed. The clamp member 3 may be bolted, welded or otherwise secured to the support 1 by any suitable means, releasable or otherwise, and an appropriate seal may be made between the clamping block 3 and the support 1. The clamp member 3 has recesses 10, 11 and 12 spaced apart along its length where the clamp member is disposed over the positions of the transducers.

In this embodiment of the invention the vane 2 is symmetrical about both a longitudinal median line and about a transverse median line, having as shown in FIG. 2 two parallel longer sides 13 and 14 and two symmetrical end sides 15 and 16. The vane may be made of steel or other suitable self supporting elastic material or combination of materials.

However, other configurations for the vane are possible. In particular, the vane may be clamped along and adjacent a side margin. However, such variants will not be described in detail.

As indicated previously, the vane is to be stimulated into vibration. A vane has two degrees of freedom, along and across the vane. The stimulation of the vane into vibration may be performed by at least one transducer, such as the transducer 20. Also, at least one sensing transducer, such as the transducers 21 and 22, are provided for sensing the vibrations of the vane. Though the positioning of the drive transducer and the sensing transducer or transducers depends largely on the configuration of the vane and the desired modes of vibration, it is normally preferable to dispose the transducers at antinodes of the dominant standing wave pattern of vibration. A preferred configuration for the present embodiment is the disposition of the transducers spaced apart along the length of the vane, preferably in the longitudinal median region thereof. In particular, as shown in FIG. 2, the drive transducer is disposed centrally of the vane and each of the sensing transducers is disposed longitudinally spaced apart from the drive transducer.

FIG. 2 illustrates particularly a preferred construction for the mounting of the transducers relative to the vane in order to provide an efficient means of inducing vibration in the vane and for sensing vibrations in it. In particular, the drive transducer 20 is disposed on a peninsular portion 17 which is formed within the vane. This peninsular portion 17 may be formed as a partly cutout flap which is thereby separated from the surrounding vane along three sides of a quadrilateral, the remaining side forming an isthmus joining the peninsular portion to the surrounding vane. The peninsular portion or flap may be of any suitable shape; the flap 17 for the drive transducer has the form of a symmetrical trapezium. Similar, square, peninsular portions, i.e., flaps 18 and 19 are provided for the mounting of the transducers 21 and 22. The transducers may be piezoelectric but other forms of transducer can be employed.

Each transducer has attached to it a fine wire 23 which may be fed along a channel in the body and through a hole in the end of the support 1 whence it can then be connected to the external circuitry.

Figure 3:
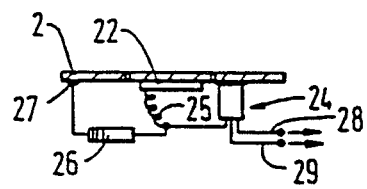
FIG. 3 illustrates a constructional detail of the embodiment of FIG. 1.

It is convenient to provide a buffer or preamplifier within the body of the instrument so as to improve the signal to noise ratio of the comparatively weak signals obtained from a sensing transducer before the signals are conveyed to an external circuit but in other configurations of the device this feature may not be required or appropriate. As shown in FIG. 3 wherein a field effect transistor 24 is disposed on the underside of the vane 2, a connecting wire 25 extends from the transducer 22 to the gate of the transistor. That gate is also connected to the vane 2 by way of a bias resistor 26, one lead of which is physically and electrically secured to the vane 2 by solder 27. The source and drain of the transistor are connected by way of leads 28 and 29 to the external circuit.

Figure 4:
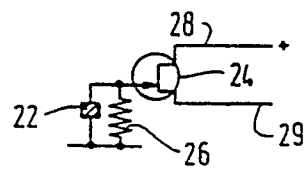
FIG. 4 illustrates an electrical circuit of the detail shown in FIG. 3.

FIG. 4 illustrates schematically the electrical network formed by the transducer 22 and the associated field effect transistor 24. In this configuration the vane 2 acts as an electrical earth.

FIG. 5 shows a cross-section through the sensor and illustrates the configuration of the vane 2 as two portions (conveniently termed fins) 2a and 2b, which in this embodiment extend laterally one to each side of the support 1.

FIG. 5 also illustrates the configuration of a flap relative to the vane and the clamping of the vane adjacent the isthmus of the flap.

As shown in FIG. 5, and also in FIG. 1, the flap 17 that carries, on one side, the drive transducer 20 also carries a substantial mass 4. The utility of this mass, which depends on the configuration and other physical attributes of the vane, will be explained with reference to FIGS. 6A to 6C.

Figure 6A:
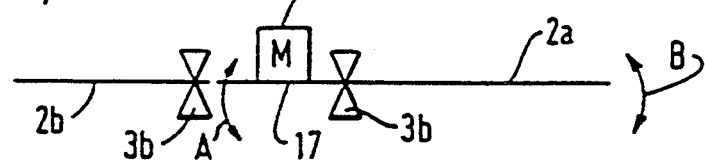
FIGS. 6A, 6B and 6C are explanatory diagrams indicating the inducing and sensing of oscillations in a vane by the particular embodiment illustrated in FIGS. 1 and 5.

FIG. 6A is a schematic diagram showing the mass 4 mounted on the flap 17, the portions 2a and 2b which are separated from each other along a line extending along the flap or peninsular portion, but are otherwise interconnected, clamps 3a and 3b adjacent each end of the peninsular portion. These clamps are constituted by the wall portions 5a and 5b of the support 1 and the adjacent parts of the clamping member 3.

The flap 17 forms by virtue of the clamp 3a a cantilever system with the adjacent portion 2a of the vane 2.

FIG. 6A illustrates the initial phase of oscillation of the vane. The drive transducer, omitted for convenience from FIG. 6A, is excited by a suitable, preferably sinusoidal, alternating signal. This excites the mass which is bonded to the flap, as shown by the double-headed arrow A. Since the flap is effectively a cantilever beam, the movement of the beam causes a reaction at the clamped part of the beam, that is to say where the vane is clamped to the support. However, because the body in relatively massive and rigid it cannot move in reaction to the vibrating cantilevered mass. Instead, the external portion 2a of the vane, which is free to move, is excited into oscillation, as shown by the double-headed arrow B. The greater the mass 4, the greater is the torque created at the clamp and the greater the corresponding amplitude of vibration of the vane.

Because the external portions 2a and 2b of the vane on each side of the body of similar mass and shape, they form a mechanically balanced resonant system. Stimulation of one fin or vane portion 2a causes a corresponding reaction in the other. If therefore the internal mass is excited at a resonant frequency of the system of fins then the fins will be excited into vibration of maximum amplitude.

Figure 6B:
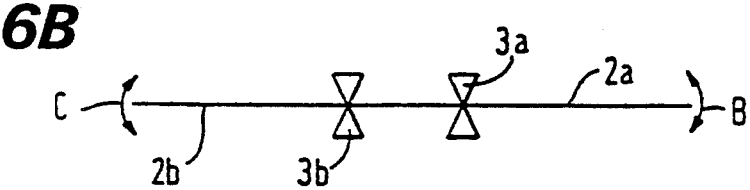

Thus in FIG. 6B, the double-headed arrow C shows the vibration of the portion 2b.

Figure 6C:
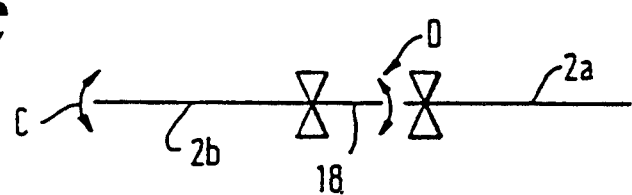

FIG. 6C shows the stimulation of a pickup flap, this being the converse of the stimulation process previously described. Movement of the external fin 2b, as shown by the double-headed arrow C, causes a reaction at the clamp 3b which, stimulates the pickup flap 18 into vibration, as shown by the double-headed arrow D.

It is obviously preferable for the peninsular portions or flaps to be as light as possible so that they require only an insignificant amount of energy for their vibration.

Figure 7:
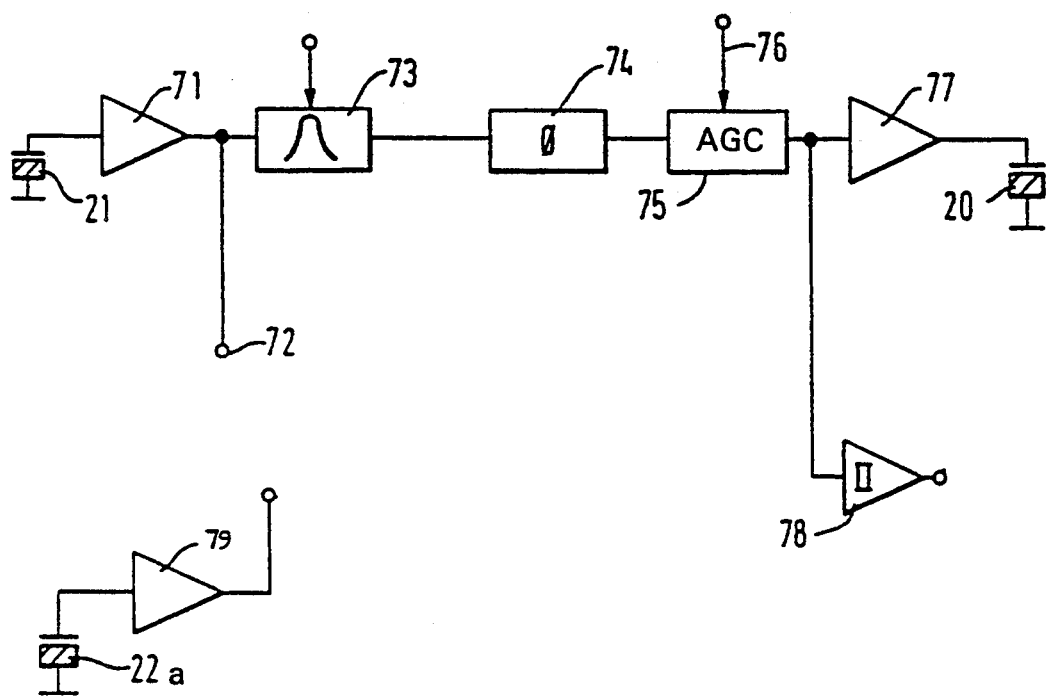
FIG. 7 is an electrical schematic diagram of a processing circuit including drive transducers and sensing transducers provided in the embodiment of FIG. 1.
Figure 8:
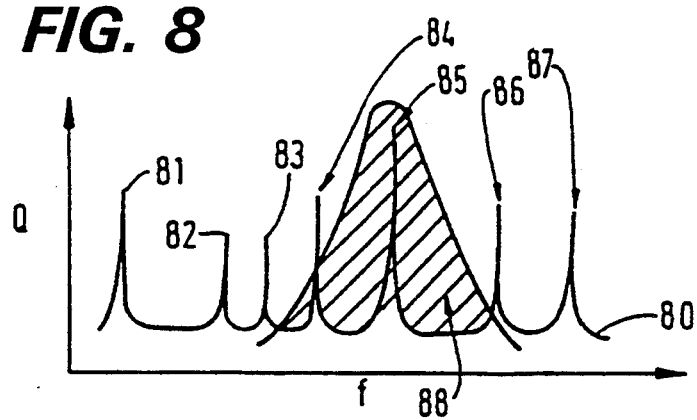
FIG. 8 illustrates in simplified form a simplified but typical frequency response of the device shown in FIG. 1.

FIG. 7 illustrates by way of example an external electrical circuit for use with the instrument; reference will first be made to FIG. 8, which illustrates a typical frequency characteristic 80 of the sensor, which is actually constituted by a set of cantilevered beams with their own resonant frequencies. FIG. 8 illustrates a resonant peak 81 corresponding to the resonant frequency of the driver flap 17, resonant peaks 82 and 83 corresponding to the resonant frequencies of the pickup flaps and other resonant peaks 84, 85, 86 and 87 corresponding to the resonant frequencies in the various modes of vibration of the vane. The frequency characteristic shown in FIG. 8 is particular to the system shown in FIGS. 1, 2 and 5. Obviously, for a different configuration of the vane there may be fewer resonant peaks or more resonant peaks.

It is in general feasible to construct the instrument so that the individual flap frequencies 81 to 83 are in a frequency range which does not overlap with the range in which fall the resonant frequencies of the parts of the vane. A similar effect can be produced by the addition of weights on the flaps to alter their resonance.

The resonant frequencies of the two fins 2a and 2b are, for similar modes, normally so close that they appear as one frequency.

There are various ways of driving the instrument. Preferably however the instrument is driven by means of a regenerative amplifier system, which is illustrated by way of example in FIG. 7.

Referring now particularly to FIG. 7, the sensing transducer 21 is coupled to an input amplifier 71. The output of this amplifier is available at a terminal 72 for use as hereinafter explained. The output of the amplifier 71 is fed through a band-pass filter 73 which may be adjustable. The pass band 88 of the filter is shown in FIG. 8 as centered on the desired resonant frequency so as to provide discrimination against all other known signals from the vane or the drive and the pickup flaps.

The output from the band-pass filter may then be adjusted for phase discrepancy by means of a phase adjuster 74. For resonance, the drive signal should be in phase with the signal at the pickup 21, Since overdriving of this system can introduce unwanted harmonics, it is preferable to provide an automatic gain control circuit 75 limiting the gain to a value set by a control 76. The output from the automatic gain control circuit is fed by way of an output amplifier 77 to the drive transducer to complete the regenerative loop.

The output of the AGC circuit 75 may also be coupled by way of a limiting amplifier 78 which provides an output indicating the frequency of the oscillating system.

The other sensing transducer 22a provides an output which is coupled by way of a respective input amplifier 79 to a respective terminal, so as to enable a phase comparison to be made between signals from the sensing transducers, representing the vibrations at the two ends of the vane or, in general, to different portions thereof.

These outputs may be used for various purposes, depending on the mode of use of the instrument. Some of these uses are described in the following.

For example, the instrument may be used to measure the density of a flowable medium in which it is immersed. The resonant frequency of vibration is given by the expression:

$$f_0 = k_1 \sqrt{\{[k_2(1-\alpha\delta t)]/(r+M_0)\}}$$

where $f_0$ is the resonant frequency at temperature t;

$\alpha$ is the thermoelastic coefficient of the material of the vane;

$\delta t$ is the difference between the ambient temperature and a calibration temperature;

r is a parameter of the density of the surrounding medium, in units of mass per unit length;

$M_0$ is a parameter of the mass of the vane, also in units of mass per unit length; and $k_1$ and $k_2$ are calibration constants at a calibrated temperature.

The parameter r, and thence the density, can be deduced if desired, by a processing circuit, by solving equation (1) if all elements of the equation are known. In practice it is possible to calibrate the instruments so that only a measurement of frequency is required.

The elastic properties of nearly all materials change with temperature and this affects the resonant frequency as shown by the above expression. However, by measuring the shift in frequency of one of the internal cantilever flaps with temperature the elasticity shift it can be deduced.

Because the mass and surrounding density of an internal flap are constant, the shift in frequency with temperature can be measured fairly easily. The resonant frequency of a flap for the sensor 21 may be measured by shifting the pass band of the pass-band filter to the region of the resonant frequency, this being measured as some calibration temperature. This frequency is expressed as $F_{cal}$. Thereafter when the instrument is being used, the control circuitry may occasionally check the frequency F of the flap. Any deviation from the calibration frequency can be attributed to a temperature shift from the calibration temperature $T_{cal}$. The ratio of the shift in these frequencies is the same as the shift of the frequencies of their fins from their calibrated temperature, so that $Fo_{cal} = f_t F_{cal}/F_t$, where $Fo_{cal}$ is the frequency of vibration of the vane corrected to the calibration temperature, $f_t$ is the frequency of vibration of the vane at the actual temperature t, $F_{cal}$ is the frequency of the flap at the calibration temperature and $F_t$ is the frequency of flap at the actual temperature t.

$F_{cal}$ is measured at the calibration stage; $F_t$ and $f_t$ are measured during the use of the instrument. The switching of the band-pass filter to measure the flap frequency can be controlled automatically by a microprocessor.

If the fins are damaged or worn, their mass may change. This will change the characteristics of the instrument, causing it to go out of calibration. It is possible to detect changes in the mass parameter $M_0$ by two methods.

According to one method, if one fin wears more than the other then two discrete resonant peaks will appear in the frequency characteristic, one for each fin. One peak will be out of phase with the other. By adjusting the phase of the drive signal it is possible to measure the resonance of the fins individually, the difference in the two frequencies being proportional to the difference in mass.

In a second method, if wear occurs equally on both fins there will be no apparent shift in relative resonant frequencies as described in the first method. However, wear will normally occur on the leading edge of a fin. Normally the two sensor pickups will provide in phase signals but if wear occurs near the leading edge of the fin then the effective mass there is reduced, causing an inbalance in the vibration. This manifests itself by a change in phase of the pickup signals as between the ends of the fins. The difference in phase is proportional to the difference in mass along the fin.

Resonant densitometers require the surrounding medium to be Newtonian, that is to say to possess a degree of elasticity or viscosity. It is possible to measure the elasticity or viscosity of a liquid by switching resonant frequencies and measuring the relative amplitudes of two resonant peaks. The use of a vibrating vane permits measurement in other modes. For example, the viscosity of the fluid surrounding the warhead presents a damping factor which reduces resonant amplitude and slightly alters the frequency. Thus, if the damping factor $C = \mu k_1$ where $k_1$ is a proportional constant and $\mu$ is the dynamic viscosity, it can be shown that the amplitude X at resonance is equal to $Fo/C\Omega_n$, where C is the damping factor, Fo is the drive signal amplitude, normally constant, and $\Omega_n$ is the resonant frequency. Thus, one can write $C = k_2/X\Omega_n$, where $k_2$ is a constant or $\mu$ is equal to $k_3/X\Omega_n$, where $k_3$ is a different constant.

The constant $k_3$ may actually shift with time due to wear, stress or other factors. These effects can be much reduced by measuring the relative amplitudes of two different frequencies. This results in the expression:

$$\mu = k_{CAL}(1/\Omega_{n1} - 1/\Omega_{n2})/(X_1 - X_2)$$

where $k_{CAL}$ is a constant of proportionality, $\Omega_{n2}$ and $\Omega_{n2}$ are two distinct resonant frequencies and $X_1$, $X_2$ are the corresponding amplitudes of vibration at those frequencies.

One particular problem especially in the offshore oil industry, is the assessment of mixture ratio. It particular applies to the determination of the quantities of natural gas liquids and water entrained in crude oil pipelines. The water content can be estimated from previously described techniques but natural gas liquids have proved almost impossible to monitor. The general measurement is called three-phase measurement because the water can be presumed to carry sediment, though this is normally removed by filters.

The viscosity of crude oil is made less by the presence of lighter components such as natural gas liquids. For example, the viscosity of crude oil is approximately 25 centi-poises whereas the viscosity of N-Pentane is approximately 0.2 centi-poises.

Using a vibrating vane as described one may measure the viscosities of crude oil ($\mu_{CRUDE}$) and a mixture of crude oil and natural gas liquid ($\mu_{MIX}$) and using a known or determined measure of the viscosity of the natural gas liquid ($\mu_{NGL}$) obtain the mixture ratio from the expression:

$$(\mu_{MIX} - \mu_{NGL})/(\mu_{CRUDE} - \mu_{NGL})$$

The viscosity of a liquid in which the instrument is immersed creates viscous damping which reduces the amplitude of a resonant peak. Measurement of the amplitude gives a measure of the damping which may be collated with the dynamic viscosity. Measuring the relative amplitude of two peaks improves the measurement by reducing the effect of long term changes in the characteristics of the sensor.

As the viscosity of the measured fluid increases, the damping effect causes a decrease in resonant frequency determined by:

$$F_n = F_o \sqrt{(1 - z^2)}$$

where $F_n$ is the damped frequency, $F_o$ is the undamped frequency and z is the damping factor.

The damping factor may be determined by the viscosity which is measured as described previously. From the measured damped frequency the undamped frequency can be derived and applied to the density equation.

Where the damping factor of the material surrounding the fins is so great that frequency measurement by self oscillation cannot be sustained then the resonant frequency can be determined by examining the phase relationship between the drive and the output signal from a sensing transducer. This is given as:

$$\tan \theta = 2z(f/f_0)/[1 - (f/f_0)^2].$$

At resonance the phase angle is 90° irrespective of the damping factor in the numerator. Observance of the frequency at quadrature will indicate resonance. This technique may also be used in circumstances of low viscosity as an alternative to regenerative driving.

Other attributes can also be measured by the instrument directly or indirectly. For example, if a dry medium has a known density which is significantly different to that of water, for example most oils, then the water content can be calculated from the line density using the equation:

$$M_m = R_w(R_b - R_d)/R_b(R_w - R_d)$$

Where $R_w$ is the water density, $R_b$ is the measured bulk density and $R_d$ is the dry density.

Some liquids exhibit a constant thermal expansion factor with temperature: this is the case for many oils. However, the temperature coefficient of water is particularly non-linear. By monitoring changes in temperature and density over a period and then differentiating with respect to temperature, the second differential yields the water content:

$$M_v = (\delta^2 R_b/\delta t^2)/(\delta^2 R_w/\delta t^2)$$

The invention could be incorporated into a sensor as described in GB-A-2222683 to enable the measurements made to be augmented by or correlated with capacitive measurements.

A further development of the invention concerns the measurement of flow rate by cross correlation. In particular, two instruments may be disposed in tandem some distance apart. In an environment where the measured attribute is changing rapidly the output waveforms from one sensor will be delayed relative to output waveforms from the other by a time T which depends on the flow rate. Using a cross correlation function the time T can be estimated and, because the distance is known, the flow rate may be found.

This function can also be applied to the density output. The density sensor can operate at significantly higher frequencies to other density transducers, for example it may operate at 12 kilohertz. The response time is inversely proportional to frequency so density signal responses of the order of 100 microseconds are possible.

Also possible is a further arrangement in which two instruments in series or tandem provide a measurement of mass/volume flowrate by frequency shift. Suppose two instruments each with a vibrating vane are disposed in series or one after the other so that one vane resonates at its natural frequency and the waves produced by the one vane activates the vane of the second instrument. If the two vanes are, for example, physically identical, they will resonate at approximately the same frequency thereby creating a tuned system. If a flowrate in the surrounding medium is introduced, the transmitted waves will experience a doppler shift at the receiver vane. The difference between the frequency transmitted by the transmitter vane and that produced by the receiver vane is approximately proportional to flow rate. Furthermore, there will be a phase difference between the transmitted and received signals also proportional to flowrate. This is more likely to be detectable under very low flow conditions.

The multiplication of volume flow rate by the density will yield mass flowrate.

I claim:

1. An instrument for the measurement of attributes of a material, comprising:
   a support;
   an elongate vane which is symmetrical about a longitudinal median line;
   means for clamping the vane to said support in a region extending along said longitudinal median line wherein said vane constitutes two similar fins in a mechanically balanced resonant system;
   a drive transducer which is disposed to induce in said vane vibration in a plane transverse said longitudinal median line; and
   at least one sensing transducer disposed to sense said vibration.

2. An instrument according to claim 1 wherein said drive transducer and said sensing transducer are each positioned in the region of the median line and are spaced apart along said median line.

3. An instrument according to claim 2 wherein at least one of said drive transducer and said sensing transducer is mounted on a peninsular portion within said vane.

4. An instrument according to claim 3 wherein said means for clamping clamps said vane at a position between said peninsular portion and an adjacent portion of said vane, said peninsular portion and said adjacent portion each constituting a cantilever.

5. An instrument according to claim 3 wherein said peninsular portion carries a substantial mass.

6. An instrument for the measurement of attributes of material, comprising:
   a support;
   a vane mounted on said support, said vane being symmetrical about a longitudinal median of said vane;
   means for clamping said vane to said support along said longitudinal median wherein said vane constitutes two similar fins in a mechanically balanced resonant system;
   a drive transducer disposed to engage said vane for inducing vibration in said vane;
   means for mounting said drive transducer to enable said transducer to induce said vibration selectively in a plane transverse said longitudinal median; and
   a sensing transducer disposed to engage said vane to sense said vibration.

7. An instrument according to claim 6 wherein said drive transducer and said sensing transducer are disposed on and spaced apart along said longitudinal median.

8. An instrument according to claim 6 wherein said means for mounting comprises a respective peninsular flap within said vane, said peninsular flap and an adjacent portion of said vane forming a cantilever system with each other.

9. An instrument according to claim 8 wherein said flap carries a substantial mass in addition to said drive transducer.

10. An instrument for the determination of attributes of a medium, comprising:
    a support;
    at least one vane mounted on said support;
    a drive transducer which is disposed relative to said vane to stimulate vibration therein;
    at least one sensing transducer disposed to sense said vibration; and
    a peninsular flap formed within said vane and constituting with an adjacent portion of said vane a cantilever system, said drive transducer being carried on said flap.

11. An instrument according to claim 10 wherein said flap also carries a substantial mass.

12. An instrument according to claim 11 wherein said vane is symmetrical about a longitudinal median, said drive transducer being disposed at a position along said median.

13. An instrument according to claim 12 and further comprising means for clamping said vane to said support along said median.

14. An instrument according to claim 13 wherein a second peninsular flap is formed within said vane, said second peninsular flap carrying said sensing transducer.

15. An instrument according to claim 14 wherein said drive transducer and said sensing transducer are spaced apart said longitudinal median.

* * * * *